United States Patent [19]

Lu et al.

[11] Patent Number: 5,391,192
[45] Date of Patent: Feb. 21, 1995

[54] AUTOMATIC VENTRICULAR PACING PULSE THRESHOLD DETERMINATION UTILIZING AN EXTERNAL PROGRAMMER AND A SURFACE ELECTROCARDIOGRAM

[75] Inventors: Richard M. T. Lu, Highlands Ranch; Bruce M. Steinhaus, Parker; Peter A. Crosby, Greenwood Village; Janice Nolan, Conifer, all of Colo.

[73] Assignee: Telectronics Pacing Systems, Inc., Englewood, Colo.

[21] Appl. No.: 205,721

[22] Filed: Mar. 4, 1994

[51] Int. Cl.6 .............................................. A61N 1/37
[52] U.S. Cl. ..................................... 607/28; 128/697
[58] Field of Search ............... 128/697, 708, 703, 704; 607/27, 28, 29, 11

[56] References Cited

U.S. PATENT DOCUMENTS

| | | | |
|---|---|---|---|
| 4,759,366 | 7/1988 | Callaghan | 607/28 |
| 4,759,367 | 7/1988 | Callaghan | 607/28 |
| 4,766,901 | 8/1988 | Callaghan | 128/419 |
| 4,903,700 | 2/1990 | Whigham et al. | 128/419 |
| 4,969,462 | 11/1990 | Callaghan et al. | 128/419 |
| 5,172,690 | 12/1992 | Nappholz et al. | 128/419 |

*Primary Examiner*—George Manuel
*Attorney, Agent, or Firm*—Gottlieb, Rackman & Reisman

[57] ABSTRACT

A clinical programming system is disclosed for use with an implanted cardiac pacemaker to automatically determine the minimum pacing energy which is necessary to evoke a ventricular depolarization. The system utilizes a series of pacing pulses of progressively decreasing energies to stimulate the ventricle, and detects evoked responses through measurements of the integrals of the R-waves provided by a surface electrocardiogram. Upon loss of capture, the minimum pacing energy is a function of the energy of the last pacing pulse which evoked a ventricular depolarization.

27 Claims, 3 Drawing Sheets

AUTOMATIC VENTRICULAR PACING PULSE THRESHOLD DETERMINATION UTILIZING AN EXTERNAL PROGRAMMER AND A SURFACE ELECTROCARDIOGRAM

FIELD OF THE INVENTION

This invention relates to implantable pulse generators or other medical devices, including tachycardia reversion devices and defibrillators, and more particularly to determining the minimum pacing energy to "capture" the ventricular chambers of a patient's heart, i.e., to cause a ventricular contraction.

BACKGROUND OF THE INVENTION

The atrial or ventricular pacing threshold is the minimum pulse energy (usually expressed as a voltage of a fixed width pulse) required to stimulate the muscle cells of the atria or ventricles to depolarize, i.e., to contract.

Pacing thresholds must be determined when the pacemaker, or other therapeutic pulse generator, is first implanted in the patient, and during subsequent follow-up examinations, to ensure that reliable "capture" is obtained while expending minimum energy. This is important since the pacemaker is battery powered and has a limited life. A conventional battery, depending on mode of operation, lead impedance, pulse amplitude, pacing rate and pulse width, may have a longevity typically ranging from four to ten years. Pulse amplitude and pulse width (which translate into energy consumed) are important factors in battery life.

Both the atrial and ventricular pacing thresholds must be measured if a dual chamber device is implanted. If a ventricular single-chamber device is implanted, then only the ventricular pacing threshold is required. If an atrial single-chamber device is implanted, then only the atrial pacing threshold is required. After a pacing threshold is measured, an appropriate pacing energy is chosen and programmed for the implanted pulse generator. The pacing energy is conventionally chosen to be two or three times the measured threshold so as to allow a safety margin for reliable capture.

Thresholds are measured at the time of implant with a pacing system analyzer when direct electrical access to the leads is possible. After implant, when the leads are not accessible, another method must be used. Conventionally, the threshold test is done with the aid of a programmer, which communicates with the implanted pulse generator via a telemetric link, at the same time that the patient's surface electrocardiogram (ECG) is viewed. Conventionally, either the atrial or ventricular threshold test starts from the previously programmed pulse amplitude and pulse width. The test is performed by automatically and progressively decreasing the pacing pulse amplitude by a fixed percent (e.g., 6%) on each test pace. The percent of decrease varies with the impedance of the lead involved. The pacing rate during the threshold test is set at a rate just above the patient's intrinsic rate to ensure that the pacing pulses will capture the heart.

When a ventricular threshold is being measured, alternate pulses are delivered at the previously programmed pacing amplitude to maintain bradycardia support. The amplitude of each decreased amplitude pulse can be annotated on the surface ECG trace. The amplitude of the last pulse to capture the heart represents the "pacing threshold." All pulses are delivered at the last programmed pulse width and pacing polarity. Unless halted manually, the test continues until either the pulse amplitude falls to a minimum predetermined voltage, or a fixed number of decreased amplitude pulses have been delivered.

The operator visually decides from the surface ECG when a loss of capture occurs, and thereupon manually terminates the test. The programmer displays the amplitude of the next-to-last pacing pulse before the termination of the test. If the test was not terminated immediately after that pulse which lost capture, the displayed amplitude will not be the true pacing pulse threshold. Therefore, the pacing pulse threshold must be confirmed by the operator by visual examination of the surface ECG. If the ECG trace is on paper, that portion of the ECG where a loss of capture occurred can be examined. If the ECG provides a trace into only a limited window of storage, then that portion of interest in the ECG may or may not be available, and the test may have to be done again. Thus, the conventional test procedure may be very time consuming. Pacing pulse thresholds also may not be determined appropriately due to operator error and this may have safety consequences for the patient.

In U.S. Pat. No. 4,969,462, issued Nov. 13, 1990 to F. J. Callaghan et al., for "Pacemaker With Improved Automatic Output Regulation", there is disclosed a threshold search by an implantable pacemaker which determines the pacing threshold by sensing the evoked potentials which follow the pacing stimuli and automatically sets the values of pacing energy accordingly. The pacing pulse is delivered between the tip electrode located inside the heart and the case of the pacemaker which is located under the skin on the patient. Sensing for evoked potentials is performed between the ring electrode located in the heart and the case. But in many patients only a unipolar lead, one with a tip electrode but no ring electrode, is available, and therefore pacing and sensing must be done through the same tip and case electrodes. In such a case, measurement of the capture threshold may not be feasible because the pacing pulse induces potentials in the immediate area of the heart which are very much greater than those resulting from a heartbeat. Until the charges resulting from the pacing pulse dissipate sufficiently, reliable sensing is impossible.

To permit sensing with the same electrodes which are used for pacing, a triphasic stimulation waveform has been described by Whigham et al. in U.S. Pat. No. 4,903,700, issued Feb. 27, 1990, for "Pacing Pulse Compensation". Here the first and third phases of the pacing pulse are of one polarity and the second phase is of the other polarity, so that the net charge to the heart muscle is zero. This allows the same electrode which conducted the pacing pulse to sense the evoked potential. Due to the different surface treatments of pacing electrodes, the procedures described by Nappholz et al. in U.S. Pat. No. 5,172,690, issued Dec. 22, 1992 for "Automatic Stimulus Artifact Reduction For Accurate Analysis of the Heart's Stimulated Response", are advantageously incorporated to optimally adjust the triphasic waveform to reduce the stimulus polarization artifact. However, optimal triphasic waveforms may still be difficult to obtain with electrodes which have very high polarization characteristics.

An evoked intracardiac ventricular potential and its integrated waveform are shown in FIGS. 5 and 6 of U.S. Pat. No. 4,766,901 issued to F. Callaghan on Aug.

30, 1988 for "Rate Responsive Pacing System Using the Integrated Evoked Potential", which is hereby incorporated by reference. This integral is used for capture classification.

Moreover, when pacing threshold searches are done routinely by the pacemaker, as described by Callaghan et al. and Nappholz et al., they may unnecessarily consume energy and shorten the life of the battery of the pacemaker due to the energy required to run the threshold searches. This is especially true today with the availability of drug-eluting leads which provide low and stable pacing thresholds.

SUMMARY OF THE INVENTION

A conventional clinical programmer with an innovative mode of operation is utilized during the implantation, and the follow-up examination, of a pacemaker to automatically determine the ventricular pacing threshold. To avoid occurrences of competition or fusion beats, or both, the pacing is done at a faster than normal rate, and the VVI or DDD (with a short AV delay) mode is used, rather than the conventional VOO mode. Further, while the surface ECG is analyzed by the programmer, the integral of the evoked ventricular depolarization potential is used, rather than the potential per se. The integral is used to minimize the effect of noise. Noise may appear as a spike on the ECG potential and be falsely characterized as representing a capture, but such a spike has little effect on the measured integral of the evoked potential. The automatic threshold test of the invention provides more consistently accurate pacing threshold measurements, improved ease of use of the programmer, and saving of operator time.

DESCRIPTION OF THE DRAWING

Further features and advantages of this invention will become apparent upon consideration of the following detailed description in conjunction with the drawing, in which.

DESCRIPTION OF THE INVENTION

Figure 1:
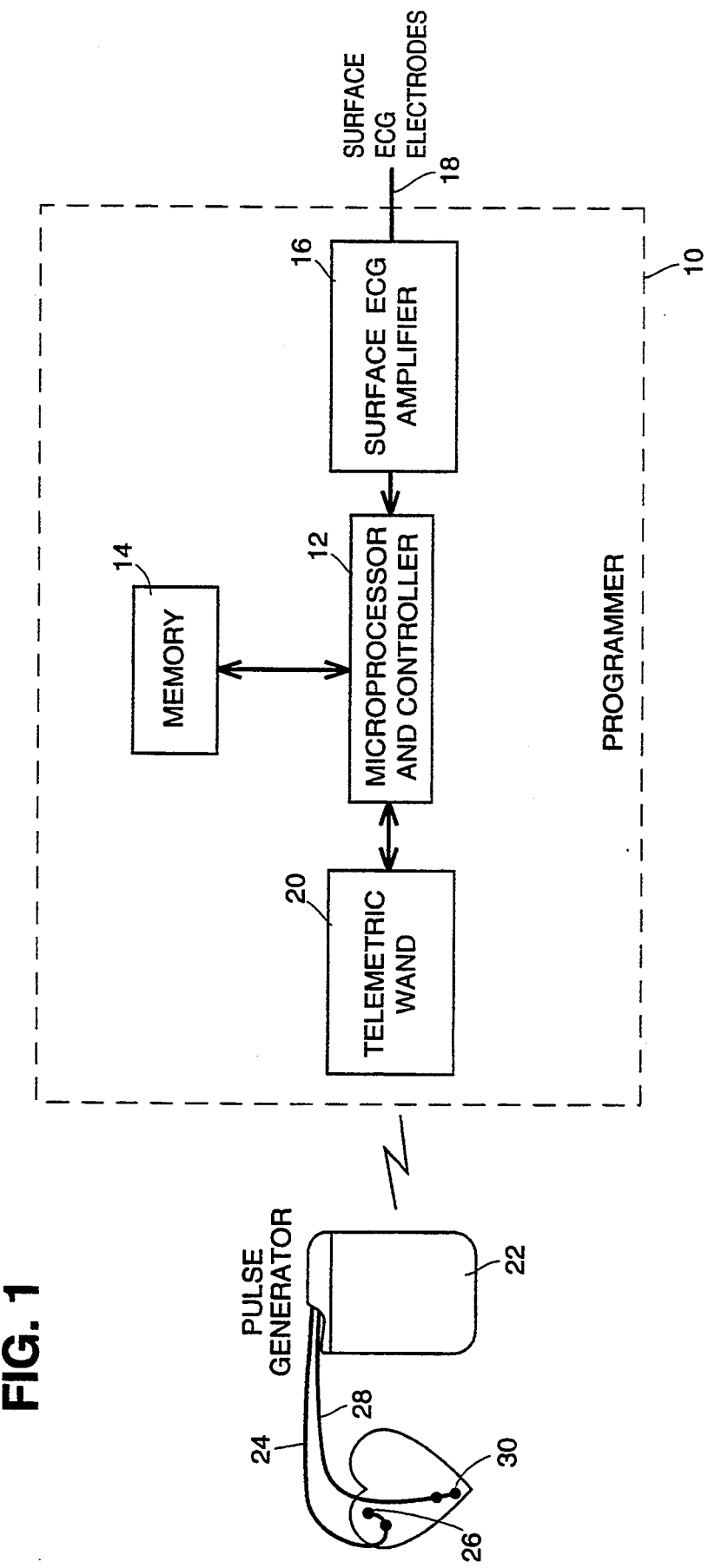
FIG. 1 is a block diagram of the hardware system of the invention including a programmer and an implanted pulse generator.

The hardware system shown in FIG. 1 comprises a programmer 10, which includes a microprocessor and controller 12, a memory 14, a surface electrocardiographic amplifier 16 having a patient cable 18 with surface ECG electrodes (not shown), and a telemetric wand 20. A pulse generator 22 (pacemaker) is implanted in the patient and is here shown as having an atrial lead 24 with an electrode 26 located adjacent to the muscle wall of the right atrium, and a ventricular lead 28 with an electrode 30 located adjacent to the muscle wall of the right ventricle. An exemplary programmer is the 9600 Network Programmer, manufactured by Telectronics Pacing Systems, Inc., which is a combined programmer/ECG monitor and recorder and has several replaceable memory cassettes which contain the operating software and data storage memory required for different pacemakers. An exemplary pulse generator is the META DDDR Model 1254 dual chamber, rate responsive, multiprogrammable, cardiac pulse generator with telemetry and a range of functions which includes fourteen pacing modes. An exemplary ventricular lead is a Telectronics Accufix Model 330-201.

The innovative test procedure is initiated by pressing an appropriate key on the programmer to cause a command, via a telemetric link which includes the programmer wand 20 and a telemetry transceiver in the pulse generator, to be issued to the pulse generator to deliver a pacing pulse sequence to the heart, at a pacing rate which is usually higher than the programmed standby rate (e.g., 100 pulses per minute), in an inhibition mode, which is VVI or DDD for a ventricular test. If the DDD mode is used, the AV delay should be sufficiently short so that ventricular pacing pulses occur before intrinsic ventricular beats otherwise would occur. The threshold tests are performed by progressively decreasing the amplitudes of alternate pacing pulses in the sequence by either a certain percentage (e.g., 6%) or a certain voltage (e.g., 0.2 v) for each pulse. (Alternatively, the pulse width may be progressively reduced, or a combination of amplitude and width may be reduced.) Following the delivery of each alternate pacing pulse, a signal is transmitted telemetrically by the pulse generator to the programmer to trigger a data acquisition mode, i.e., the analysis of the surface electrocardiographic waveform which is input from the surface ECG amplifier 16, and telemetered main timing events for capture classification. Only alternate waveforms, corresponding to reduced amplitude pacing pulses, are analyzed.

Figure 2:
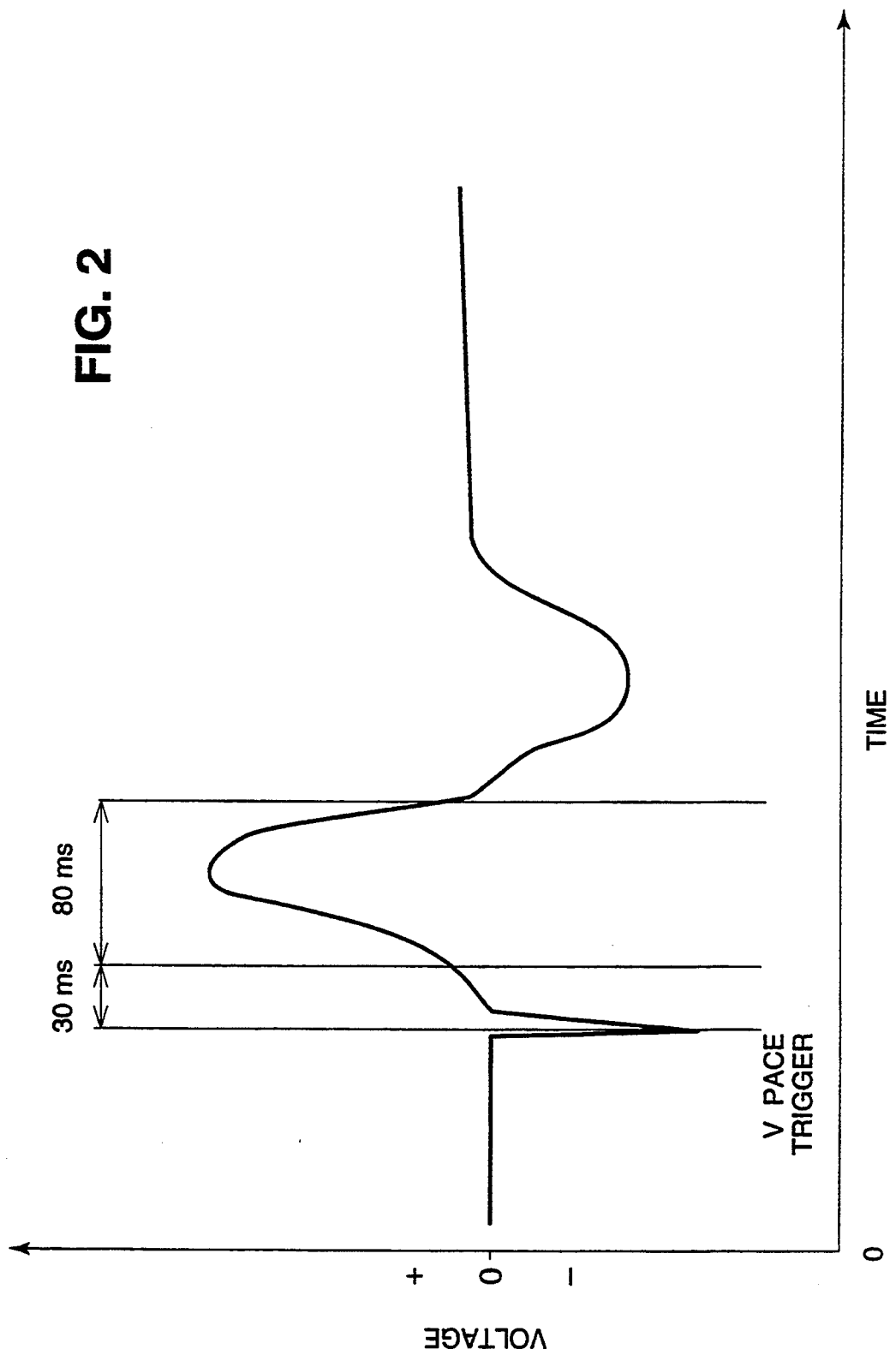
FIG. 2 is a trace of an evoked ventricular depolarization potential.

FIG. 2 shows an exemplary ventricular surface electrogram with an initial, negative, V-pace trigger, and a subsequent positive R-wave. Depending on the lead and amplifier arrangements, these polarities may be different. The total time of the window in which the system deals with the electrogram is 110 ms, but only the waveform in the approximately 80 ms following an initial 30 ms of blanking is actually integrated and utilized by the system.

Figure 3:
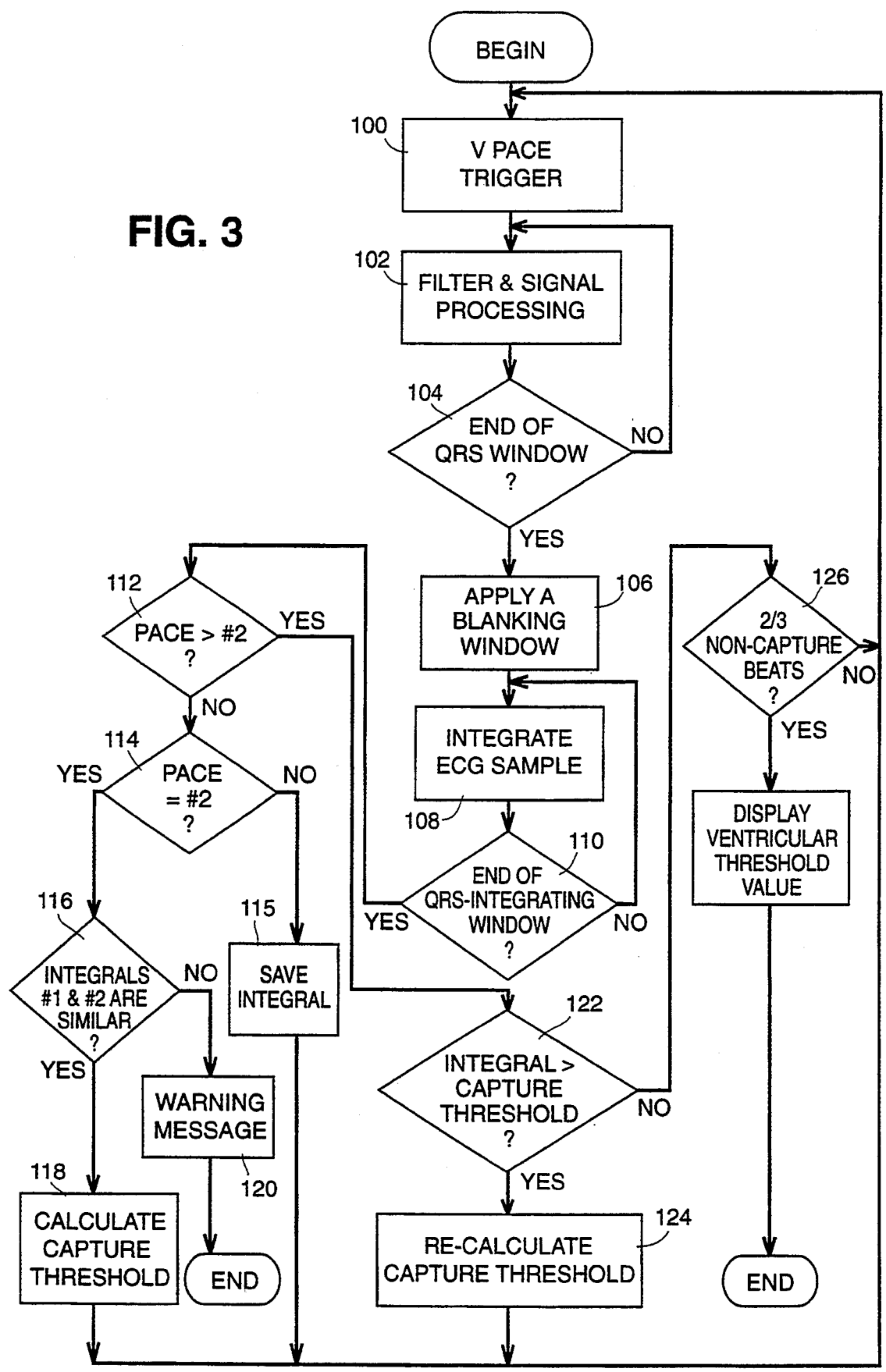
FIG. 3 is a flow chart of the algorithm utilized in the system of FIG. 1 to automatically determine the ventricular pacing pulse threshold.

FIG. 3 shows the logic diagram for determining the ventricular capture threshold utilizing the electrogram waveform shown in FIG. 2.

Following a V-pace trigger (step 100), and for 110 ms following the pacing pulse of FIG. 2, the R-wave signal from the surface ECG is extended to a digital filter and signal processing block 102 which includes, e.g., a 17-Hz low pass filter to reduce the effect of noise interference, digital notch filters to remove line frequencies of 50 and 60-Hz, signal squaring, etc., all of which are known techniques to remove baseline offset and noise frown the ventricular signal. The time interval of the 110 ms window is determined in step 104 by sampling the signal at a predetermined rate and counting and passing the quantity of samples required for 110 ms. The initial quantity of samples comprising the initial 30 ms of the signal, which contains the V-pace trigger, as shown in FIG. 2, is blanked out in step 106. The initial 30 ms of the waveform is passed through the filter and signal processing block 102 because otherwise the start of the subsequent 80 ms of waveform might generate initial transients in the filtering process. The samples comprising the 80- ms part of the waveform, which represents the principal interval (QRS) of the evoked R-wave, if in fact any such waveform was evoked, are integrated (digitally, by summing the samples) at step 108. The end of the combined QRS (R-wave) and blanking window at step 110 stops this integration.

After the ventricular threshold test is initiated, the integrals from the first two test pulses are compared. In step 112, a check is made whether more than two test pulses have been generated. If not, then in step 114 the current pulse number is checked to see whether it is the second pulse. If it is not, then it must be the first pulse, and the integral of this first waveform is stored in step 115, and the next pulse is awaited. If it is the second pulse, then both of the first two integrals are checked for similarity in step 116. If the integrals are similar, e.g., the integral of the second evoked QRS waveform is within a range of +100% to −50% of the integral of the first evoked QRS waveform, and both integrals are above a predetermined default value, then capture is assumed for the first two test pacing pulses. If capture is assumed, then a percentage (e.g., 50%) of the average of the first two integrals will be used to establish the initial capture threshold in step 118 for the subsequent V-pace pulses.

If the first two integrals are not similar, then it is assumed that at least one pulse did not capture the heart and the same procedure is repeated for the next two V-pace pulses, but the entire test now employs a faster pacing rate. The assumption is that at least one pulse did not capture; by increasing the rate, i.e., overdriving the ventricle still faster, intrinsic beats are less likely. If the test still fails, the pacing rate may be increased further, up to the maximum allowable pacing rate. If that also fails, higher initial amplitudes may be tried in a similar sequence. The initial test pacing pulse amplitude, at the start of the process, is typically the programmed value; only if there is no capture at the start of the test when using the fastest pacing rate is a higher amplitude used. A failure at the beginning of the test for all initial pacing rates and amplitudes gives rise to a warning message in step 120 and the test is aborted.

Assuming that the first two integrals are similar, then following the next test pacing pulse, which has a decremented amplitude, step 122 is executed. There it is determined whether or not the integral of this next evoked (QRS) R-wave is greater than the initial capture threshold which is set to a percentage of the average of the prior two capture integrals. If it is greater, then in step 124 the capture threshold is recalculated as a function of the average of all of the prior capture integrals (e.g., 50% of the average), and the next test pacing pulse is awaited. But if it is less, and if this makes it two out of the last three integrals representing non-capture, then in step 126 the last stored V-pace pulse amplitude which evoked an R-wave is displayed and the procedure is ended. But if so far the last two out of three test pulses (in general, X out of Y test pulses) have not failed to capture, then the next pulse, which will have a decremented amplitude, will be generated.

This loop continues until the last two out of three test pulses represent non-captures. It should be noted that all prior capture pulses are taken into consideration in determining the dynamic capture threshold for the next pulse, since the R-wave is not consistent in its amplitude for each pulse, and the cumulative average accommodates this inconsistency. Thus, the programmer, by controlling a series of V-pace test pulses, of progressively smaller amplitudes, and integrating the principal interval (QRS) of the R-waves which are evoked, can automatically determine the ventricular threshold.

A similar test can be performed by telemetering out the ventricular intracardiac electrogram and operating on it. The reason that operating on the surface ECG is preferred, despite the fact that its amplitude may not be consistent, is that intracardiac telemetry requires charge balancing as described above and this may be difficult to achieve for some high polarization leads.

Although the invention has been described with reference to a particular embodiment, it is to be understood that this embodiment is merely illustrative of the application of the principles of the invention. For example, while it is traditional to generate programmed-amplitude pulses between successive test pulses, to ensure bradycardia backup support in case of a loss of capture, it may not be necessary to do so in the invention because capture by every test pulse is verified. However, backup pacing is advantageous toward the end of the test sequence where loss of capture occurs (during the X out of Y procedure), although it is possible to lower the amplitude of each backup pulse to the most recent confirmed capture amplitude. Also, instead of integrating R-wave signals and averaging them to form a new threshold, other kinds of R-wave signal processing may be employed to form a composite which is thereafter the new threshold. Thus it is to be understood that numerous modifications may be made in the illustrative embodiment of the invention and other arrangements may be devised without departing from the spirit and scope of the invention.

What is claimed is:

1. A method of externally determining the minimum energy of a pacing pulse necessary to evoke a ventricular depolarization response in the heart of a patient, comprising the steps of:

providing a series of test pacing pulses of sequentially decreasing energy to the heart;

obtaining the depolarization potential signal evoked by each pulse on a surface electrocardiogram;

providing for each pacing pulse a sample interval for the respective depolarization potential signal;

integrating each depolarization potential signal during its sample interval;

determining whether or not the first two sample interval integrals represent similar evoked depolarization potential signals and, if they do, then averaging said first two sample interval integrals and taking a fraction thereof as the capture threshold;

determining whether or not each succeeding sample interval integral is larger than said capture threshold and, if it is, then averaging the prior sample interval integrals and the current sample interval integral and taking a fraction thereof as the new capture threshold;

determining that a pacing pulse did not evoke a depolarization response if its sample interval integral is not larger than the capture threshold then in effect; and responsive to pacing pulses no longer evoking depolarization response, registering the energy of the last pacing pulse whose respective sample interval integral was larger than the capture threshold then in effect.

2. A method according to claim 1 wherein it is determined that test pacing pulses are no longer evoking depolarization responses when N sample interval integrals out of the last M sample interval integrals are not larger than the respective capture thresholds then in effect.

3. A method according to claim 2 wherein N is two, M is three, and said fraction is one-half.

4. A method according to claim 2 wherein if the first two sample interval integrals do not represent similar evoked depolarization potential signals, then the initial series of test pacing pulses is terminated and a second series of test pacing pulses is commenced at a higher rate.

5. A method according to claim 4 wherein sample interval integrals are considered to represent similar evoked depolarization potential signals if the second sample interval integral is within +100% to −50% of the first sample interval integral.

6. A method according to claim 4 wherein the depolarization potential signal during each sample interval is filtered, and thereafter an initial subinterval of the filtered signal is blocked and only the remaining subsequent subinterval of the filtered signal is integrated to provide the sample interval integral.

7. A method according to claim 1 wherein if the first two sample interval integrals do not represent similar evoked depolarization potential signals, then the initial series of test pacing pulses is terminated and a second series of test pacing pulses is commenced at a higher rate.

8. A method according to claim 7 wherein sample interval integrals are considered to represent similar evoked depolarization potential signals if the second sample interval integral is within +100% to −50% of the first sample interval integral.

9. A method according to claim 1 wherein sample interval integrals are considered to represent similar evoked depolarization potential signals if the second sample interval integral is within +100% to −50% of the first sample interval integral.

10. A method according to claim 1 wherein the depolarization potential signal during each sample interval is filtered, and thereafter an initial subinterval of the filtered signal is blocked and only the remaining subsequent subinterval of the filtered signal is integrated to provide the sample interval integral.

11. A method of determining the minimum energy of a pacing pulse necessary to evoke a ventricular depolarization comprising the steps of:
providing a series of test pacing pulses of sequentially decreasing energy to the heart of a patient;
integrating the R-wave in the cardiac signal following each test pacing pulse;
determining whether a first group of capture R-wave integrals are similar and, if they are, then averaging such integrals and taking a fraction thereof as the capture threshold;
determining whether each succeeding integral is larger than said capture threshold and, if it is, then averaging the prior capture R-wave integrals and the new integral and taking a fraction thereof as the current capture threshold;
determining when a pacing pulse fails to evoke a capture R-wave response; and
registering the minimum energy as a function of the last pacing pulse whose respective R-wave integral was larger than the capture threshold then in effect.

12. A method according to claim 11 wherein it is determined that test pacing pulses are no longer evoking capture R-wave responses when N sample integrals out of the last M sample integrals are not larger than the respective capture thresholds then in effect.

13. A method according to claim 11 wherein if the first group of R-wave integrals are not similar, then terminating the initial series of test pacing pulses and starting a second series of test pacing pulses at a higher rate.

14. A method according to claim 11 wherein integrals are considered similar if the second integral is within +100% to −50% of the first integral.

15. A method according to claim 11 wherein each R-wave is filtered, and thereafter an initial subinterval of the filtered R-wave is blocked and the remaining subsequent subinterval of the R-wave is integrated.

16. A method of determining the minimum energy of a pacing pulse necessary to evoke a ventricular depolarization comprising the steps of:
providing a series of test pacing pulses of sequentially decreasing energy to the heart of a patient;
integrating the R-wave in the cardiac signal following each pacing pulse;
averaging successive capture R-wave integrals and taking a fraction thereof as the capture threshold;
determining whether each succeeding integral is larger than said capture threshold and, if it is, then averaging the prior capture integrals and the new integral and taking a fraction thereof as the current capture threshold;
determining when a test pacing pulse fails to evoke a capture R-wave response; and
registering the minimum energy as a function of the last test pacing pulse whose respective capture integral was larger than the capture threshold then in effect.

17. A method according to claim 16 wherein it is determined that test pacing pulses are no longer evoking R-wave responses when N sample integrals out of the last M sample integrals are not larger than the respective capture thresholds then in effect.

18. A method according to claim 16 wherein each R-wave is filtered, and thereafter an initial subinterval of the filtered R-wave is blocked and only the remaining subsequent subinterval of the R-wave is integrated.

19. Apparatus for determining the minimum energy of a pacing pulse necessary to evoke a ventricular depolarization comprising:
means for providing a series of test pacing pulses of sequentially decreasing energy to the heart of a patient;
means for integrating the R-wave in the cardiac signal following each pacing pulse;
means for averaging successive R-wave integrals and taking a fraction thereof as the capture threshold;
means for determining whether each succeeding integral is larger than said capture threshold and, if it is, then averaging the prior integrals and the new integral and taking a fraction thereof as the current capture threshold;
means for determining when a test pacing pulse fails to evoke an R-wave response; and
means for registering the minimum energy as a function of the last test pacing pulse whose respective integral was larger than the capture threshold then in effect.

20. Apparatus in accordance with claim 19 wherein said means for determining when a test pacing pulse fails to evoke an R-wave response operates by determining that N sample integrals out of the last M sample integrals are not larger than the respective capture thresholds then in effect.

21. Apparatus in accordance with claim 19 wherein said integrating means operates to filter each R-wave, and thereafter to block an initial subinterval of the filtered R-wave and to integrate only the remaining subsequent subinterval of the R-wave.

22. A method of determining the minimum energy of a pacing pulse necessary to evoke a ventricular depolarization comprising the steps of:
providing a series of test pacing pulses of sequentially decreasing energy to the heart of a patient;
processing the R-wave signal following each test pacing pulse;
determining whether a first group of capture R-wave signals are similar and, if they are, then forming a composite of such signals and taking a fraction thereof as the capture threshold:
determining whether each succeeding R-wave signal is larger than said capture threshold and, if it is, then forming a composite of the prior capture R-wave signals and the new R-wave signal and taking a fraction thereof as the current capture threshold;
determining when a test pacing pulse fails to evoke a capture R-wave response; and
registering the minimum energy as a function of the last pacing pulse whose respective R-wave signal was larger than the capture threshold then in effect.

23. A method according to claim 22 wherein it is determined that test pacing pulses are no longer evoking capture R-wave responses when N sample R-wave signals out of the last M sample R-wave signals are not larger than the respective capture thresholds then in effect.

24. A method according to claim 22 wherein if the first group of capture R-wave signals are not similar, then terminating the initial series of test pacing pulses and starting a second series of test pacing pulses at a higher rate.

25. A method of determining the minimum energy of a pacing pulse necessary to evoke a ventricular depolarization comprising the steps of:
providing a series of test pacing pulses of sequentially decreasing energy to the heart of a patient;
processing the R-wave signal following each test pacing pulse;
forming a composite of successive capture R-wave signals and taking a fraction thereof as the capture threshold;
determining whether each succeeding R-wave signal is larger than said capture threshold and, if it is, then averaging the prior capture R-wave signals and the new R-wave signal and taking a fraction thereof as the current capture threshold;
determining when a test pacing pulse fails to evoke a capture R-wave response; and
registering the minimum energy as a function of the last test pacing pulse whose respective capture R-wave signal was larger than the capture threshold then in effect.

26. A method according to claim 25 wherein it is determined that test pacing pulses are no longer evoking capture R-wave responses when N sample R-wave signals out of the last M sample R-wave signals are not larger than the respective capture thresholds then in effect.

27. A method according to claim 25 wherein each R-wave is filtered, and thereafter an initial subinterval of the filtered R-wave is blocked and only the remaining subsequent subinterval of the R-wave is processed.

* * * * *